United States Patent [19]
Bertho et al.

[11] Patent Number: 5,688,930
[45] Date of Patent: Nov. 18, 1997

[54] PROCESS FOR THE PREPARATION OF SURFACE ACTIVE AGENTS USING WHEAT BY-PRODUCTS AND THEIR APPLICATIONS

[75] Inventors: Jean-Noël Bertho; Philippe Mathaly; Véronique Dubois, all of Reims; Régis de Septfontaines De Baynast, Versailles, all of France

[73] Assignee: Agro Industrie Recherches et Developpements, Pomacle, France

[21] Appl. No.: 519,543

[22] Filed: Aug. 25, 1995

[30] Foreign Application Priority Data

Aug. 30, 1994 [FR] France ................................ 94 10406

[51] Int. Cl.$^6$ ........................ C07G 3/00; C07H 15/04; A61K 31/70
[52] U.S. Cl. ........................ 536/18.6; 536/4.1; 536/18.5; 514/25; 514/844
[58] Field of Search ........................ 536/18.6, 4.1, 536/127; 514/25, 844

[56] References Cited

U.S. PATENT DOCUMENTS

| | | | |
|---|---|---|---|
| 3,839,318 | 10/1974 | Mansfield | 260/210 R |
| 4,350,766 | 9/1982 | Mehlberg | 435/161 |
| 4,950,743 | 8/1990 | McCurry, Jr. et al. | 536/18.6 |
| 5,104,585 | 4/1992 | Fabry et al. | 510/470 |
| 5,286,406 | 2/1994 | Scholz et al. | 510/158 |

FOREIGN PATENT DOCUMENTS

| | | |
|---|---|---|
| 0 265 111 | 4/1988 | European Pat. Off. |
| 94 21655 | 9/1994 | WIPO |

*Primary Examiner*—John Kight
*Assistant Examiner*—Everett White
*Attorney, Agent, or Firm*—Pearne, Gordon, McCoy & Granger LLP

[57] ABSTRACT

Processes for preparing mixtures of alkyl pentosides from wheat by-products, such as wheat bran, wheat fibre or wheat straw are provided. The resulting mixtures are useful as surfactants. Compositions containing the resulting surfactants agent are also provided.

9 Claims, No Drawings

PROCESS FOR THE PREPARATION OF SURFACE ACTIVE AGENTS USING WHEAT BY-PRODUCTS AND THEIR APPLICATIONS

BACKGROUND OF THE INVENTION

The present invention relates to the processes of preparing mixtures of alkyl pentosides from wheat by-products, to their applications and to their formulations, in particular as surface active agents.

The grafting of alkyl groups on carbohydrates gives surface active agents with very interesting surface properties and generally good levels of biodegradability (R. D. Swisher, *Surfactant Biodegradation*, Marcel Dekker, Inc., New York, 1987).

The most usual reaction is the glycosylation of fatty alcohols by intermediary glycosides or pentosides. This is carried out using an acid catalyst and the alkyl glycosides thus obtained are stable over a wide pH range, especially neutral and basic. The substrate which is most often used as the reducing sugar is glucose. Glycosylation carried out using this sugar gives alkyl glucoside and polyglucoside mixtures which are known for their surface active properties. These have a great number of applications in such varied fields as detergents, the chemical and parachemical industries or in the fields of medicine and biology (see, for example, WO 93 07160, WO 93 072491, DE 42 12 080 AI, U.S. Pat. No. 4,987,225).

Large quantities of glucose are required in order to prepare these alkyl glucosides. Obtaining this glucose from, for example, wheat flour, requires numerous stages. The gluten must be removed and the glucose purified, in particular by filtration stages and chromatography on ion exchange resins.

The main disadvantage of this approach is the high cost of the raw material, which is due in particular to the use of expensive agricultural materials, such as flour and the numerous stages required to purify the glucose. This obviously limits the potential applications for these processes. In addition, the glycosylation of the glucose or other hexoses is carried out at high temperatures (100° to 150° C.), which stains the products.

SUMMARY OF THE INVENTION

The aim of the invention is to obtain surface active agents from a particularly cheap raw material by a few simple operating stages, which do not require the use of high temperatures which cause staining.

According to the invention, wheat bran or fibre or even wheat straw is used as the raw material for the preparation of surface active agents.

Wheat bran may be used in its unprocessed state, but it is preferable to use de-starched wheat bran, as described in the European Patent Application No. 401 117.

Wheat fibre may also be used. The term wheat fibre refers to the compounds obtained during a fractionating process, in particular used to produce starch and gluten in accordance with the following description:

Wheat ground in a mill produces flour and brans. The relatively high rate of extraction (from 75% to 90%) causes part of the brans to be mixed with the flour. A paste is then made by mixing the flour with water at ambient temperature and with a dry ingredient content of approximately 45%. The paste is then re-diluted to a dry ingredients content of approximately 35%, then separated into the three main compounds, i.e. starch, gluten and soluble substances. This separation stage may be carried out by a three-phase decanting process, or by any other process such as the MARTIN processes and their derivatives. The starch is then sieved to separate the bran particles which are mixed in with it. The residue from the sieve is therefore mainly made up of brans and residual starch. In the present invention, these mixtures are referred to as wheat fibers. Fractions from the sieving of wastes from gluten, which are also made up of brans and starch are also referred to a wheat fibers. More generally, according to the present invention, any material derived from the transformation of wheat and which is composed of brans and possibly starch is referred to as wheat fibre. The bran itself is made up of hemicellulose, formed from xylose and arabinose monomers and cellulose.

The invention also relates to a process for preparing surface active agents, characterized in that it consists in bringing wheat bran or fibre, or even wheat straw into contact with an aqueous acid solution between 20° and 150° C. and preferably between 60° and 120° C., for at least five seconds in order to obtain a pentose syrup, where necessary removing the solid pulp from the pentose syrup, and in bringing the pentose syrup from which the pulp has been removed into contact with an alcohol having between 6 and 22 carbon atoms at a temperature of between 20° and 150° C., and preferably between 30° and 110° C., until a solution of surface active pentosides is obtained, and in separating the surface active pentosides from this solution.

This process has the advantage of using sugars which are currently of little value, of working with mixtures of these sugars and, as a result, of avoiding the purification stages.

DETAILED DESCRIPTION OF THE PREFERRED EMBODIMENTS

The term pentose syrup refers to a syrup which in the case of straw and bran from which the starch has been removed, contains 60% to 75% pentoses and 40% to 250% hexoses. This term also refers to a syrup which may sometimes contain up to 65% glucose where the wheat fibre and bran has not been de-starched, but which nevertheless contains a significant proportion of pentoses.

The syrup is mainly made up of pentoses, especially D-xylose and L-arabinose, which have the advantage of being more reactive during glycosylation. This property allows grafting under managed conditions, avoiding in particular any deterioration in the reagents or the products of the reaction. In contrast to the preparation of alkyl polyglucosides and glucosides which requires temperatures above 120° C. (see DE 42 12 080, WO 93 07160), the synthesis of alkyl pentosides according to the present invention may be carried out at a temperature below 100° C.

In addition, the glycosylation may be carried out without the use of additional acid catalysts; the acidity of the syrup provides the catalyst for the reaction.

The first stage of the process according to the invention consists in bringing the wheat bran or fibre or even wheat straw into contact with an aqueous acid solution. The polysaccharides which are present in the unprocessed, de-starched or de-lignified wheat fibre or bran or the straw are extracted, solubilized and hydrolysed in an aqueous acid medium. The acid used may be hydrochloric acid, sulfuric acid, phosphoric acid, a sulfonic acid such as benzene-sulfonic acid, paratoluene-sulfonic acid, camphor-sulfonic acid, sulfosuccinic acid or an alkyl sulfosuccinate such as decyl or lauryl sulfosuccinate, perhalohydric acids, such as, for example, perchloric acid.

This contact is generally made for 5 to 90 minutes in a simple mixer. But the contact time may be reduced to several seconds using a device called a "jet cooker," which allows the mixing to be carried out in line.

Where wheat straw or bran is used, the second stage of the process according to the invention consists in removing the solid pulp from the pentose syrup. This operation may be carried out by pressing at a pressure in the order of $2.10^5$–$500.10^5$ Pascals and preferably in the order of $5.10^5$–$60.10^5$ Pascals by means of a screw press, filter press or any other equipment which can squeeze the juice from the wet pulp.

Where necessary, the pulp may be re-diluted with two to four times their volume of water and pressed on the same press as that used for the first pressing. This operation is not essential, but it increases the yield of pentoses extracted. In order to increase the concentration of pentoses, all or part of the raw acidic juice may be recycled to hydrolyse wheat fibers or brans or wheat straw a second time. This recycling will increase the content of dry materials in the juice and reduce the amount of acid required to extract the pentoses by 30%.

The impurities contained in the pentose juice may also be precipitated using chelating salts. For example, metallic cations such as aluminum hydroxide, aluminum sulfate, alkaline-earth cations such as magnesium, calcium, strontium or barium hydroxides, magnesium, calcium, strontium or barium sulfates and magnesium, calcium, strontium or barium chlorides.

In order to facilitate the removal of the precipitated solid pulp and impurities from the pentose syrups, the juice obtained may be centrifuged using equipment which will remove the insoluble substances from the juice, such as a horizontal decanter, a filter press, a static decanter, tangential filtration systems or a self-cleaning plate centrifuge.

The pentose solution or juice may be demineralized by chromatography on at least one ion exchange resin, by low-pressure exclusion chromatography, by electrodialysis or even by a combination of these methods, whilst leaving, in preference, at least 0.02 $H^+$ equivalent per mole of pentoses in order to avoid the need to add an acid as the catalyst. In chromatography, the pentose fraction is mixed with one part of the salt fraction. On the ion exchange resin, it passes from a cation exchange resin to an anion exchange resin, the quantity of anion exchange resin being at least 0.02 $H^+$ equivalents less than the stoichiometry.

The pentose syrup may also be concentrated by evaporation of up to 30%–95% and more particularly 60%–80% of the dry material. The pentose syrup from which the solid pulp has been removed is generally between 50% and 95% pure pentose in relation to the dry material.

The third stage of the process according to the invention consists in bringing the pentose syrup from which the solid pulp has been removed into contact with an alcohol having from 6 to 22 carbon atoms. The alcohol has the formula $R^1OH$, $R^1$ being a branched or linear alkyl radical from 6 to 22 carbon atoms, a hydrocarbonic radical having from 1 to 4 ethylenic non-saturations and from 6 to 22 carbon atoms or one of these radicals substituted by 1 to 3 substituents on different carbon atoms chosen from amongst the following: hydroxy, halogen and trifluoromethyl. Preference is given to fatty alcohols with from 8 to 16 carbon atoms; in particular of octanol and decanol mixtures, decanol and dodecanol mixtures, dodecanol and tetradecanol mixtures, and dodecanol, tetradecanol and hexadecanol mixtures. In general a ratio of 1 to 4 equivalents of alcohol to sugar is used.

However, at first it is preferable to carry out glycosylation of a short alcohol by the pentoses of the syrup. Following this, transglycosylation by fatty alcohols with the formula $R^2OH$ is carried out. The short alcohol has the formula $R^2OH$, $R^2$ being a linear alkyl radical having from 1 to 5 carbon atoms. It is preferable to carry out this glycosylation in the total absence of solvents, but where necessary it is possible to use a solvent such as an ethyl oxide, i.e. tetrahydrofuran, diethyl oxide, 1,4-dioxane, isopropyl oxide, methyl-tert-butyl ether, ethyl-tert-butyl ether or diglyme; a halogenated hydrocarbon such as methylene chloride, chloroform, 1,2-dichloroethane; a nitrated solvent such as nitromethane, nitro-2-propane; a solvent from the amide family such as N-methylformamide, N,N-dimethylformamide, N,N-dimethylacetamide, N-methyl-2-pyrrolidone, a nitrile such as acetonitrile, an alkane such as hexane, heptane or octane, or a high-aromatic solvent such as toluene or xylene. It is preferable to carry out this reaction at a temperature of between 30° and 110° C. in order to avoid staining the product as far as possible, but it is possible to carry out the process at a temperature of up to 150° C. Where the pentose juice has been completely demineralized, an acidic catalyst must be added to the reaction medium in the ratio of 0.1% to 5% by mass of the dry material of the syrup. This acid may be hydrochloric acid; sulfuric acid, phosphoric acid; a sulfonic acid such as benzene-sulfonic acid, paratoluene-sulfonic acid, camphor-sulfonic acid, sulfosuccinic acid; an alkyl sulfosuccinate such as decyl or lauryl sulfosuccinate; or perhalohydric acids, such as, for example, perchloric acid. This acidic catalysis may also be carried out by 0.05 to 6 equivalents by weight of a sulfonic resin in its $H^+$ form or an acid resin. It is preferable to prevent total demineralization of the juice obtained from pressing, thus avoiding the need to add an acidic catalyst.

The process for collecting the alkyl pentoside mixture consists in:

removing the solvent from the reaction, where this is present, neutralizing the acidity of the initial syrup or acidic catalyst, then filtering the obtained salt. Neutralization is carried out, for example using a hydrogen carbonate or an alkaline or alkaline-earth metal carbonate, in particular sodium hydrogen carbonate, or by an alkaline or alkaline-earth metal hydroxide, in particular soda, purifying the required product:

by evaporation of the excess fatty alcohol in a vacuum of between 0.001 and 10 mbars at a temperature of between 60° and 250° C., or by chromatography on a column of silica gel, aluminum or active carbon or on an ion exchange resin, or by crystallization in a solvent or a mixture of suitable solvents chosen from ethyl oxides such as tetrahydrofuran, diethyl oxide, 1,4-dioxane, isopropyl oxide, methyl-tert-butyl ether, ethyl tert-butyl ether or diglyme; a halogenated hydrocarbon such as methylene chloride, chloroform, 1,2-dichloroethane; a nitrated solvent such as nitromethane, nitro-2-propane; a solvent from the amide family such as N-methylformamide, N,N-dimethylformamide, N,N-dimethylacetamide, N-methyl-2-pyrrolidone; a nitrile such as acetonitrile; an alkane such as hexane, heptane or octane; or a high-aromatic solvent such as toluene or xylene, or by selective extractions by solvents which are immiscible in water.

The isolated product then has a residual percentage of fatty alcohol of between 0% and 5%, preferably between 0% and 1%, where necessary solubilizing the surfactant in water in order to obtain a surfactant composition having a dry material content of 20% to 80%, if necessary bleaching this solution by adding from 0.05% to 10% and preferably between 0.5% and 3% of hydrogen peroxide, peroxodisulfates of alkaline or alkaline-earth metals, perborates, persulfates, perphosphates, percarbonates, ozone or even periodinates at a temperature of between 15° and 100° C. It is preferable to use 30% or 50% hydrogen peroxide. The bleaching agent used in the present invention should obviously be compatible with all the ingredients, of the final formulation and with the applications of use of the finished products.

In practice, the process consists in mixing de-starched or unprocessed wheat fibre or bran, with a granule size of between 0.8 and 1.5 mm, or wheat straw with a granule size of between 0.8 and 150 mm in size with at least twice its volume of water containing acid in a ratio of 0.01% to 15% and more specifically 1% to 10% of the dry material of the straw, bran or wheat fibre. It is preferable to use sulfuric acid, hydrochloric acid or sulfosuccinic acid, homogenizing then heating the medium to a temperature of between 20° and 150° C., preferably between 60° and 120° C. for between 1 and 60 minutes, where wheat straw or bran is being used, pressing the mixture at a pressure in the order of $2.10^5$ to $500.10^5$ Pascals and preferably in the order of $5.10^5$ to $60.10^5$ Pascals by means of a screw press, filter presses or any other equipment which will squeeze the juice from the wet pulp. This operation allows the juice 1 to be separated from the pulp 1, where necessary diluting the pulps 1 with at least three times their volume of water and pressing them in the same press as that used for the first pressing. This operation is not essential, but it increases the yield of pentoses extracted. The juice 2 and pulp 2 are then separated, mixing the juice from the pressing process (juice 1 and juice 2), where necessary recycling all or part of the raw acidic juice 2 in order to hydrolyse brans, straws or other wheat fibers again, preferably with a similar quantity of raw acidic juice as in the first dilution. It is possible to recycle the juice in this manner several times, allowing wheat fibre or bran or straw to be hydrolysed without adding more water, as only the quantity of acid is adjusted, where necessary precipitating the impurities contained in the pentose juice using chelating salts. For example, metallic cations such as aluminum hydroxide, aluminum sulfate alkaline-earth cations such as magnesium, calcium, strontium or barium hydroxides, magnesium, calcium, strontium or barium sulfates, magnesium, calcium, strontium and barium chlorides, where necessary centrifuging the juice obtained using equipment which will remove the insoluble substances from the juice, such as a horizontal clarifier, a filter press, a static clarifier, tangential filtration systems or a self-cleaning plate centrifuge. This will give a juice 3 from which the insoluble substances have been removed and a paste which constitutes from 0.5% to 3% of the total volume before separation and a dry material representing 4.5% of the initial dry material, where necessary demineralizing the juice by chromatography on an ion exchange resin, by acid-type low-pressure exclusion chromatography, by electrodialysis or even by precipitation of the anions contained in the juice using chelating salts, concentrating the juice 3 by evaporation of up to 20%–80% and preferably from 60%–80% of the dry material. The syrup has a pentose content of between 50% and 90% of the dry material, glycosylation is carried out using alcohol.

The mixtures of alkyl pentosides according to the invention have very interesting properties and are of particular use in the fields of detergents, cosmetics and foodstuffs.

These mixtures of alkyl pentosides make remarkable non-ionic surface active agents. They have particularly interesting solutizing, emulsifying, foaming, wetting and dispersant properties. They may be used as detergents, in particular in compositions for washing powders and products for washing dishes, floors and windows, as softeners and detergent admixtures in these compositions, in both liquid and powder form. They may also be added to hair care products or toothpastes and can be used in cosmetics as beauty care ointments, creams and lotions for softening and toning the skin as a gentle surfactant which does not irritate the skin or the mucous membranes. Their foaming and softening properties may also be used to advantage in foam bath preparations. They may also be included in the formulation of foodstuffs as additives for oil and fat, in mayonnaise, salad creams and sauces. In industry they may be used as agents for carrying out polymerization in dispersion and emulsion. They are also substances which can form vesicles and have liquid crystal properties.

Some of the most useful of these properties are their ability to lower the surface tension, particularly of water and their foaming, emulsifying and detergent power.

Amongst the derivatives of the invention, those with the best foaming power are the ones in which $R^1$ is an alkyl and in particular an alkyl with from 6 to 14 carbon atoms, preferably from 8 to 12 and ideally 10 carbon atoms, which have a higher foaming power of than that of similar conventional products. Testing was carried out in accordance with the standard NFT 73404 which consists in pouring 500 ml of the surfactant solution at a constant rate into a graduated thermostatically controlled 1000 ml test tube containing 50 ml of the same solution. The quantity of foam generated by the flow was estimated by volume just after the flow has stopped and then a time dependent evaluation was made of the stability of the foam after 20 minutes. The mixtures of decyl-dodecyl pentosides have a higher foaming power than that of the surface active agents which are currently most frequently used, such as sodium dodecyl benzene sulfonate (SDBS), sodium dodecyl sulfate (SDS), sodium lauryl ethersulfate with 2 mole of ethylene oxide (LES) or dodecyl betaine.

With the compounds according to the invention, the initial volume of foam is 530 ml, whereas with the others it is below 450 ml. Their foaming power is also higher than that of alkyl polyglucosides (APG). In addition, the stability of the foam produced by these compounds is very good over time as the percentage loss is generally less than 5% after 20 minutes.

The alkyl pentoside mixtures according to the invention lower the surface tension of water very effectively. This property was tested using a conventional technique for measuring surface tension, with a Schlumberger Tensimat tensiometer No. 3. The measurement was carried out at 25° C. The measurement was made using a rectangular strip of platinum (25 mm×5 mm). When $R^1$ has less than 12 carbon atoms, this lowering of the surface tension of the water is higher than that observed in conventional products (SDBS, SDS, LES, APG). This makes the emulsification of any dirt on the clothes much easier during washing.

The compounds with the best emulsifying properties are those in which $R^1$ is an alkyl, in particular an alkyl with from 8 to 22 carbon atoms and preferably with 14 to 20 carbon atoms.

Finally, it should be noted that the alkyl pentosides according to the invention are fully biodegradable and do not endanger the environment, whilst having a high level of stability.

The present invention therefore also relates to a process for giving surface active properties to a composition, characterized in that it consists in incorporating in the said composition from 0.1% to 60% by weight of a derivative or mixture of derivatives according to the invention.

The compounds according to the invention may be in various forms, in particular in the form of liquid or powdered detergents; foaming or non-foaming lotions; liquid or semi-liquid emulsions such as lotions obtained by dispersion of a fatty phase in an aqueous phase or vice-versa; suspensions or emulsions with a soft consistency, such as creams or ointments; gels or even solid preparations such as cleansing bars, impregnated pads, or in the form of moisturizing face masks.

Water, organic solvents suitable for topical application, such as acetone, isopropyl alcohol, fatty acid triglycerides $C_6-C_{24}$, glycol ethers such as alkyl ethers below mono- or dialkylene glycol, with an alkylene radical of 2 to 4 carbon atoms can be used as a vehicle for the compositions according to the invention.

Polyalkylene glycol esters and a short chain acid, $C_1-C_4$, or even volatile silicones may also be used as the solvent.

The compositions according to the invention may also contain fatty substances such as natural or synthetic oils.

The compositions according to the invention may also contain thickening or gelling agents such as cellulose or cellulose derivatives. The thickening agents may also be acrylic polymers, alginates, gums such as xanthane, guar or carob gum or gum arabic or even polyethylene glycols, bentonites and montmorillonites.

The compositions according to the invention may also contain active materials such as moisturizing agents, as well as admixtures such as antioxidants, preservatives, colorings and perfumes.

The compositions according to the invention may also be in the form of solutions or dispersions containing alkyl pentosides in vesicular form, these vesicles then being used as encapsulating agents for the active lipophile and/or hydrophile ingredients.

One detergent mixture in powder form according to the invention includes from 0.1% to 60% and preferably from 10% to 30% by weight of a detergent base and from 99.9% to 40%, and preferably from 90% to 70% by weight of admixtures.

The detergent base may be a derivative or a mixture of derivatives according to the invention. It may also be a mixture of one or more derivatives according to the invention with one or more conventional surfactants used in this application; these surfactants may also be anionic, nonionic, cationic or amphoteric. The proportion of surfactants according to the invention constitutes from 1% to 100% by weight and preferably from 50% to 100% of the charge of surfactants.

The powdered detergent composition was used at a concentration of 1 to 20 g/l and preferably between 1 and 6 g/l.

Washing was carried out in a conventional machine, at a temperature of 20° to 80° C., preferably between 20° and 60° C., for a period of 10 to 60 minutes.

A liquid detergent composition according to the invention consists of 0.1% to 60%, and preferably from 10% to 60% by weight of a detergent base and from 99.9% to 40% and preferably from 90% to 70% by weight of admixtures.

The liquid detergent base may be a derivative or a mixture of derivatives according to the invention. It may also be a mixture of one or more derivatives according to the invention with one or more conventional surfactants used in this application.

The liquid detergent composition according to the invention is used in an aqueous solution at a concentration of 6 to 12 g/l, and at temperatures of 40° to 70° C.

The detergent compositions may contain the types of additives described below:

Other surface active agents in quantities corresponding to 3% to 40% by weight in relation to the detergent mixture, surface active agents such as:

anionic surface active agents alkylester sulfonates with the formula R—CH($SO_3$M)—COOR' where R represents an alkyl radical $C_{8-20}$, preferably $C_{10}-C_{16}$; R' is an alkyl radical $C_1-C_6$, preferably $C_1-C_3$ and M is an alkaline cation (sodium, potassium, lithium), substituted or unsubstituted ammonium (methyl-dimethyl-, trimethyl-, tetramethylammonium, dimethylpiperidinium . . . ) or a derivative of an alkanolamine (monoethanolamine, diethanolamine, triethanolamine . . . ). Of particular interest here are methyl ester sulfonates, the R radical of which is C14–C16;

alkylsulfates with the formula ROSO$_3$M, where R represents an alkyl or hydroxyalkyl radical $C_{10}-C_{24}$, preferably $C_{12}-C_{20}$, and especially $C_{12}-C_{18}$, M represents a hydrogen atom or a cation of the same type as above, as well as their ethoxylene (OB) and/or propoxylene (OP) derivatives, having on average from 0.5 to 6 unit cells and preferably from 0.5 to 3 OE and/or OP unit cells;

alkylamide sulfates with the formula RCONHR'OSO$_3$M, where R represents an alkyl radical C2–C22, preferably C6–C20, R' represents an alkyl radical C2–C3, M represents a hydrogen atom or a cation of the same type as above, as well as their ethoxylene (OE) and/or propoxylene (OP) derivatives, having on average from 0.5 to 60 OE and/or OP unit cells;

alkyl-D-galactoside uronates with the following formula:

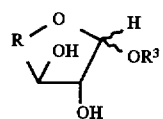

$R^3$ being a linear or branched alkyl radical from 6 to 22 carbon atoms and preferably from 8 to 16 carbon atoms, a hydrocarbonic radical having from 1 to 4 ethylenic non-saturations and from 6 to 22 atoms of carbon or one of these radicals substituted by 1 to 3 substituents on different carbon atoms chosen from hydroxy, halogen or trifluoromethyl, R being

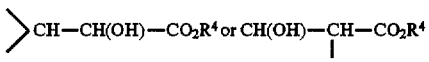

of which the carbon carrying the hydroxy group is not linked to the endocyclic oxygen atom. $R^4$ being hydrogen, an alkaline metal or alkaline-earth metal atom or a quaternary ammonium group;

salts of saturated or unsaturated fatty acids $C_8$–$C_{24}$, preferably $C_{14}$–$C_{20}$, alkyl benzene sulfonates $C_9$–$C_{20}$, primary or secondary alkyl sulfonates $C_8$–$C_{22}$, alkyl glycerol sulfonates, sulfonated polycarboxylic acids as described in GB A-1 082 179, paraffinsulfonates, N-acyl N-alkyltaurates, alkylphosphates, alkylisethionates, alkylsuccinamates, sulfosuccinates, N-acyl sarcosinates, alkyl glycoside sulfates, polyethoxycarboxylates, the cation being an alkaline metal (sodium, potassium, lithium) a substituted or non-substituted ammonium residue (methyl-, dimethyl-, trimethyl-, tetramethylammonium, dimethylpiperidinium . . . ) or a derivative of alkanolamine (monoethanolamine, diethanolamine, triethanolamine . . . );

non-ionic surface acting agents polyoxyalkyl alkylphenols (polyethoxyethylenes, polyoxypropylenes, polyoxybutylenes) of which the substituent alkyl is $C_6$–$C_{12}$ and containing from 5 to 25 oxyalkylene unit cells; an example of these are TRITON X-45, X-114, X-100 or X-102 marketed by Rohm & Haas Cy.;

glucosamides, glucamides;

glycerolamide derivatives of N-alkylamines (U.S. Pat. No. 5,223,179 and FR A-1,585,966);

polyoxyalkylened aliphatic alcohols $C_8$–$C_{22}$ containing from 1 to 25 oxyalkylene unit cells (oxyethylene, oxypropylene); an example of these are TERGITOL 15-S-9, TERGITOL 24-L-6 NMW marketed by Union Carbide Corp., NEODOL 45-9, NEODOL 23-65, NEODOL 45-7, NEODOL 45-4 marketed by Shell Chemical Cy., KYRO EOB marketed by The Procter and Gamble Cy.;

products obtained from the condensation of ethylene oxide with a hydrophobic compound resulting from the condensation of propylene oxide with propylene glycol, such as PLURONIC, marketed by BASF;

products obtained from the condensation of ethylene oxide, the compound resulting from the condensation of propylene oxide with ethylene diamine, such as TETRONIC marketed by BASF;

amine oxides such as dimethylamine alkyl oxides $C_{10}$–$C_{18}$, alkoxy oxides C8–C22, ethyl dihydroxy ethylamines;

alkylpolyglycosides described in U.S. Pat. No. 4,565,647;

fatty acid amides C8–C20;

ethoxylated fatty acids;

ethoxylated fatty amides;

ethoxylated amines cationic surface active agents alkyl dimethylammonium halides;

amphoteric and zwitterionic surface active agents alkyl dimethylbetaines, alkylamidopropyldimethylbetaines, alkyltrimethylsulfobetaines, products from the condensation of fatty acids and protein hydrolysates.

BUILDER AGENTS, in quantities corresponding to approximately 5%–50% and preferably from 5%–30% by weight for liquid detergent formulas, or approximately 10%–80% and preferably 15%–50% by weight for powdered detergent formulas, builder agents such as:

inorganic builders polyphosphates (tripolyphosphates, pyrophosphates, orthophosphates, hexametaphosphates) of alkaline metals, ammonium or alkanolamines;

tetraborates or borate precursors;

silicates, in particular those having a $SiO_2/Na_2O$ ratio in the order of 1.6/1 to 3.2/1 and lameliar silicates as described in U.S. Pat. No. 664,839;

alkaline or alkaline-earth carbonates (bicarbonates, sesquicarbonates);

co-granules of hydrated silicates of alkaline metals and alkaline metal carbonates (sodium or potassium) rich in silicon atoms in the form Q2 or Q3, as described in EP A-488 868;

crystalline or amorphic amino silicates of alkaline metals (sodium, potassium) or ammonium, such as zeolites A, P, X . . . ; zeolite A with a particle size in the order of 0.1–10 micrometers is preferred.

organic builders water-soluble polyphosphonates (ethane 1-hydroxy-1,1-diphosphonates, salts of methylene diphosphonates . . . );

water-soluble salts of carboxylic polymers or copolymers or their water-soluble salts such as:

polycarboxylate ethers (oxydisuccinic acid and its salts, monosuccinic acid tartrate and it salts, disuccinic acid tartrate and its salts);

hydroxypolycarboxylate ethers;

citric acid and its salts, mellitic acid, succinic acid and their salts;

salts of polyacetic acids (ethylene diamine tetraacetates, nitrilotriacetates, N-(2 hydroxyethyl)-nitrilodiacetates);

alkyl succinic acids C5–C20 and their salts (2-dodecenylsuccinates, lauryl succinates);

carboxylic polyacetal esters polyaspartic acid, polyglutamic acid and their salts;

polyimides derived from the condensation polymerization of aspartic acid and/or glutamic acid;

polycarboxymethylated derivatives of glutamic acid or other amino acids.

These builders may be used in a mixture of various proportions. The proportion of builders to the surface active base as a whole is between 1 and 4 and preferably between 2 and 3.

The OPTICAL BRIGHTENERS are those conventionally used in this application, in particular disulfonic stilbene acid or the derivatives of di-(styryl)diphenyl.

BLEACHING AGENTS in quantities of approximately 0.1%–20% and preferably approximately 1%–10% by weight, possibly accompanied by BLEACHING ACTIVATORS in quantities of approximately 0.1%–60%, and preferably approximately 0.5%–40% by weight, agents and activators such as:

bleaching agents perborates such as monohydrated or tetrahydrated sodium perborates;

peroxygenated compounds such as peroxyhydrated sodium carbonate, peroxyhydrated pyrophosphate, peroxyhydrated urea, sodium peroxide, sodium persulfate, preferably accompanied by a bleaching activator generating carboxylic peroxy acid during the washing process; amongst these activators the following are of interest:

tetraacetylethylene diamine, tetraacetylmethylene diamine, tetraacetyl glycoluryl, p-acetoxybenzene sodium sulfonate, glucose pentacetyl, lactose octacetyl . . . ;

percarboxylic acids and their salts (called "percarbonates") such as hexahydrated magnesium monoperoxyphthalate, magnesium metachloroperbenzoate, 4-nonylamine-4-oxoperoxybutyric acid, 6-nonylamine-6-oxoperoxycaproic acid, diperoxydodecanedioic acid peroxysuccinic acid nonylamide, decyldiperoxysuccinic acid.

These agents may be used in association with at least one of the dirt-repelling or anti-redeposition agents as described below. Non-oxygenated bleaching agents may also be used; these act by photoactivation in the presence of oxygen, i.e. agents such as sulfonated aluminum and/or zinc phthalocyanines.

DIRT REPELLING AGENTS, in quantities in the order of 0.01%–10% and preferably approximately 0.1%–5% and in particular in the order of 0.2%–3% by weight, such as:

cellulose derivatives such as cellulose hydroxyethers, methylcellulose, ethylcellulose, hydroxypropyl methylcellulose, hydroxybutyl methylcellulose;

polyvinyl esters grafted onto polyalkylene trunks such as polyvinyl acetates grafted onto polyoxyethylene trunks (EP A-219 048);

polyvinyl alcohols;

polyester copolymers based on ethylene terephthalate and/or propylene terephthalate and polyoxyethylene terephthalate unit cells, with an ethylene terephthalate and/or propylene terephthalate/polyoxyethylene terephthalate mole ratio (number of unit cells) in the order of 1/10 to 10/1, preferably in the order of 1/1 to 9/1, the polyoxyethylene terephthalates having polyoxyethylene units with a molecular weight in the order of 300 to 5000, preferably in the order of 600 to 5000 (U.S. Pat. No. 3,893,929; U.S. Pat. No. 4,116,896; U.S. Pat. No. 4,702,857; U.S. Pat. No. 4,770,666);

sulfonated polyester oligomers obtained by sulfonation of an oligomer derived from ethoxylated allyl alcohol, from dimethylterephthalate and from 1,2 propylene diol, presenting from 1 to 4 sulfonated groups (U.S. Pat. No. 4,968,451);

polyester copolymers based on propylene terephthalate cell units and polyoxyethylene terephthalate and completed by ethyl or methyl cell units (U.S. Pat. No. 4,711,730) or polyester oligomers completed by alkylpolyethoxy groups (U.S. Pat. No. 702,857) or anionic sulfopolyethoxy (U.S. Pat. No. 4,721,580) or sulfoaroyl (U.S. Pat. No. 4,877,896) groups;

polyesters-polyurethanes obtained by the reaction of a polyester with a molecular mass of 300–4000 obtained from adipic acid and/or terephthalic acid and/or sulfoisophthalic acid and a diol with a mass of less than 300, on a prepolymer with isocyanate end groups obtained from a polyoxyethylene glycol with a molecular mass of 600–4000 and a diisocyanate (FR A-2 334 698).

ANTI-REDEPOSITION AGENTS, in a quantity of approximately 0.01%–10% by weight for a powdered detergent composition, approximately 0.01%–5% by weight for a liquid detergent composition, agents such as:

ethoxylated monoamines or polyamines, ethoxylated amine polymers (U.S. Pat. No. 4,597,898, EP A-11 984);

carboxymethylcellulose;

sulfonated polyester oligomers obtained by condensation of isophthalic acid, diethylene glycol and dimethyl sulfosuccinate (FR A-2 926);

polyvinyl pyrrolidones;

iron and magnesium CHELATING AGENTS in quantities in the order of 0.1%–10% and preferably in the order of 0.1%–3% by weight, agents such as:

aminocarboxylates such as nitrilotriacetates, ethylenediaminetetraacetates, hydroxyethylethylenediaminetriacetates;

aminophosphonates such as nitrilotris-(methylene phosphonates);

polyfunctional aromatic compounds such as dihydroxydisulfobenzenes.

POLYMERIC DISPERSING AGENTS, in quantities in the order of 0.1%–7% by weight, used to control the calcium and magnesium hardness, agents such as:

water-soluble salts of polycarboxyl acids with a molecular mass in the order of 2000 to 100,000, obtained by polymerization or copolymerization of ethylenically unsaturated carboxylic acids such as acrylic acid, maleic acid or anhydride, fumaric acid, itaconic acid, aconitic acid, mesaconic acid, citraconic acid, methylene malonic acid, and, in particular, polyacrylates with a molecular mass in the order of 2000–10000 (U.S. Pat. No. 3,308,067), acrylic acid and maleic anhydride copolymers with a molecular mass in the order of 5,000–75,000 (EP A-66 915);

polyethylene glycols with a molecular mass in the order of 1000 to 50,000.

BRIGHTENERS in quantities of approximately 0.05%–1.2% by weight, agents such as derivatives of stilbene, pyrazoline, coumarin, fumaric acid, cinnamic acid, azole, methinecyanines, thiophenes . . . (*The Production and Application of Fluorescent Brightening Agents*, M. Zahradnik, published by John Wiley & Sons, New York, 1982.)

ANTI-FOAMING AGENTS, in quantities of up to 5% by weight, agents such as:

monocarboxylic fatty acids C10–C24 or their alkaline salts, ammonium or alkanolamines, fatty acid triglycerides;

saturated or unsaturated aliphatic, alicyclic, aromatic or heterocyclic hydrocarbons such as paraffins and waxes;

N-alkylaminotriazines;

monostearylphosphates, monostearyl alcohol phosphates;

polyorganosiloxane oils or resins, where necessary combined with silica particles.

SOFTENING AGENTS, in quantities of approximately 0.5%–10% by weight, agents such as clays.

ENZYMES in quantities of up to 5 mg by weight, preferably in the order of 0.05–3 mg of active enzyme/g of detergent composition, enzymes such as:

proteases, amylases, lipases, cellulases, peroyxdases (U.S. Pat. No. 3,553,139; U.S. Pat. No. 4,101,457; U.S. Pat. No. 4,507,219; U.S. Pat. No. 4,261,868).

OTHER ADDITIVES such as:

alcohols (methanol, ethanol, propanol, isopropanol, propanediol, ethylene glycol, glycerine);

buffer agents;

perfumes;

pigments.

The invention also relates to the use of derivatives according to the invention in order to obtain a detergent composition for washing dishes and for household use. This composition is comprised of 1% to 50% by weight and preferably from 5% to 30% of a mixture according to the invention and 99% to 50% by weight, and preferably from 95% to 70% by weight of admixtures or other surfactants.

Amongst the anionic surface active agents present there may be alkylsulfates, alkyl ethersulfates, alkyl sulfonates, alkyl benzenesulfonates, soaps, alkyl ethercarboxylates, N-acylsarcosinates, alkyl isethionates, N-acyl N-alkyltaurates, alkylphosphates, alkyl sulfosuccinates, alkyl sulfosuccinamates, sulfonated derivatives of fatty acids . . . Alkyl-D-galactoside uronates with the following formula may also be used:

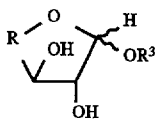

$R^3$ being a linear or branched alkyl radical from 6 to 22 carbon atoms and preferably from 8 to 16 carbon atoms, a hydrocarbonic radical having from 1 to 4 ethylenic non-saturations and from 6 to 22 atoms of carbon or one of these radicals substituted by 1 to 3 substituents on different carbon atoms chosen from hydroxy, halogen or trifluoromethyl, R being

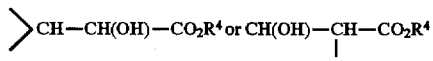

of which the carbon carrying the hydroxy group is not linked to the endocyclic oxygen atom. $R^4$ being hydrogen, an alkaline metal or alkaline-earth metal atom or a quaternary ammonium group.

Amongst the non-ionic surface active agents present there may be amine oxides, alkylglucamides, alkylpolyglycosides, oxyalkyl derivatives of fatty alcohols such as PLANTAREN® marketed by HENKEL . . .

In addition to non-ionic surface active agents of the present invention there may also be present in the compositions of washing up liquids other additives or surfactants such as:

amphoteric and zwitterionic surface active agents such as alkyl diemethylbetaines, alkyl amidopropylbetaines, alkyl sultaines, products from the condensation of fatty acids on proteins or protein hydrolysates, amphoteric derivatives of alkylpolyamines such as AMPHIONIC XL® marketed by RHONE-POULENC, AMPHOLAC 7T/X® and AMPHOLAC 7C/X® marketed by BEROL NOBEL;

bactericidal or disinfectant agents such as triclosan;

synthetic cationic polymers such as MIRAPOL A550®, MIRAPOL A15®, marketed by RHONE-POULENC, MERQUAT 550® marketed by CALGON . . . ;

polymers used to control the viscosity of the mixture and/or the stability of the foams generated during use, such as cellulose or guar derivatives (carboxymethylcellulose, hydroxyethylcellulose, hydroxypropylguar, carboxymethylguar, carboxymethylhydroxypropylguar . . . );

hydrotropic agents such as short alcohols C2–C8, in particular ethanol, diols and glycols such as diethylene glycol, dipropylene glycol . . . ;

hydrating or moisturizing agents for the skin, such as glycerol, urea; skin protection agents, such as proteins or protein hydrolysates; cationic polymers, such as cationic derivatives of guar (JAGUAR C13S®, JAGUAR C162®, HICARE 1000® marketed by RHONE-POULENC);

colorants, perfumes, preservatives . . .

The compounds according to the invention are pleasant to the touch and are easily rinsed off.

The invention also relates to a cosmetic composition consisting of between 0.1% to 50% and preferably from 5% to 35% by weight of the surface active agent and from 99.9% to 50% and preferably from 95% to 65% by weight of an admixture or active ingredient, characterized in that from 0.5% to 100% of the surface active agents are at least one mixture of the invention.

The non-ionic surfactants to which this invention relates may be used more particularly in the formulations of cosmetic lotions, make-up removing creams, skin care creams or creams or lotions for protection against the sun or ultraviolet rays, mousses, hair styling gels or any other formulation used for hair styling or conditioning, hair or body shampoos, face or body cleansing gels, liquid soaps, foam bath preparations, formulations used for cleaning the teeth or mouth such as toothpastes or mouthwashes. The non-ionic surfactants of the present invention may also be used alone or together with others in the formulation of toilet tablets or soaps.

The cosmetic compositions generally contain surface active agents used to disperse, emulsify, solubilize or stabilize the various compounds used for their active ingredients or emollient or moisturizing properties. These active ingredients may include enzymes, vitamins, antioxidants, antimicrobic and anti-dandruff agents . . .

The moisturizing agents may include glycerol, sorbitol, urea, collagen, gelatine, aloe vera, hyaluronic acid . . .

The emollients used are generally chosen from alkyl monoglycerides, alkyl diglycerides, triglycerides such as oils extracted from plants and vegetables (palm, copra, cottonseed, soya, sunflower, olive, grape seed, sesame, groundnut, caster oils . . . ) or oils derived from animal origins (tallow, fish oils . . . ), derivatives of these oils such as hydrogenated oils, synthetic oils such as poly-α-olefins, derivatives of lanoline, mineral or paraffinic oils, perhydrosqualene, squalene, diols such as 1,2-propanediol, 1,3-butanediol, cetyl alcohol, stearyl alcohol, oleic alcohol, polyethylene glycols or polypropylene glycols, fatty esters such as isopropyl palmitate, ethyl-2-hexyl cocoate, myristyl myristate, lactic acid esters, stearic acid, behenic acid, isostearic acid, silicone fluids which group cyclic polydimethylsiloxanes, hydroxylated α-ω polydimethylsiloxanes, trimethylsilyl α-ω polydimethylsiloxanes, polyorganosiloxanes such as polyalkylmethylsiloxanes, polymethylphenylsiloxanes, polydiphenylsiloxanes, amine derivatives of silicones, silicone waxes, copolyether silicones (such as SILBIONE 70646® oil marketed by RHONE-POULENC or DC 190® marketed by DOW CORNING) or mixed silicone derivatives such as copoylyether polyalkylmethylsiloxane-silicone mixed copolymers.

To these compounds may be added mineral powders or particles such as calcium carbonate, mineral oxides in powder or colloidal form (particles smaller or in the order of one micrometer, sometimes several tens of nanometers), such as titanium dioxide, silica, salts of ammonium generally used as antiperspirants, kaolin, talc, clays and their derivatives . . .

Preservatives such as methyl, ethyl, propyl and butyl hydroxybenzoic acid esters, sodium benzoate, GERMABEN® or any other chemical agent for preventing bacterial growth or molds which are traditionally used in cosmetic compositions are generally added to these compounds in a quantity of 0.01% to 3% by weight.

As an alternative to these chemical agents it is sometimes possible to use agents which modify the activity of water and greatly increase the osmotic pressure, such as carbohydrates or salts.

In order to protect the skin or hair from the sun or UV rays, solar filters may be added to these formulations, these being either chemical compounds which largely absorb UV rays, such as the approved compounds listed in the European Directive No. 76/768/EEC, its appendices and the subsequent amendments to this directive, or titanium dioxide or cerium oxides in powdered or colloidal form. Perfumes, colorants or pigments may also be added. Viscosing or gelling polymers (such as cross-linked CARBOPOL® polyacrylates marketed by GOODRICH), cellulose derivatives such as hydroxypropylcellulose, carboxymethylcellulose, guars and their derivatives, carob, tara or cassia gum, xanthane gum, alginates, carragheens, chitin derivatives such as chitosan may also be present . . .

Toothpaste may contain, in addition to abrasive agents such as silica or calcium carbonate (used at 5% to 25% by weight of the total of the composition), from 0.1% to 5% by weight of the said surfactants of the invention, either singly or in a mixture with conventional surfactants such as anionic, non-ionic or zwitterionic surfactants such as alkylbetaines, alkylamidopropylbetaines, amphoterics or mixtures of these compounds. These surface active agents are used as foaming agents during use of the composition, as well as for their cleaning and disinfecting powers. Sometimes they are used specifically for their "medicinal" properties, for example alkyl sarcosinates which protect the teeth and inhibit the enzymatic action of the bacteria responsible for tooth or gum disease. The toothpaste compositions also include from 5% to 85% of so-called humectant agents such as glycerol, sorbitol, polyethyleneglycols, lactilol and xylitol.

The rheological behavior of toothpaste, i.e. its viscosity, its behavior on the brush, ease of extrusion from the tube or dispenser, the flow of the paste, is controlled by thickening agents, such as certain silicas used for this purpose (TIXOSIL 43® marketed by RHONE-POULENC) and/or polymers used alone or in combination with xanthene gum, guar gum, cellulose derivatives (carboxymethylcellulose for example), cross-linked polyacrylates such as CARBOPOL® marketed by GOODRICH, alginates or carragheens and VISCARIN®. The total amount of thickening agents constitutes from 0.1% to 15% by weight of the composition of a toothpaste.

In general, along with these various constituents there are usually medicinal agents such as certain fluorine or potassium salts, flavorings, sweetening agents and water.

The surfactants of this invention may also be used in the formulations of toilet tablets known as soaps.

The conventional compositions of toilet tablets generally include fatty acid salts used together with the surfactants of the invention and where necessary surfactants other than fatty acid salts or fatty acids themselves. These compositions may not even contain any fatty acid or fatty acid salt and their formulations are then based on other surfactants, such as, for example, sodium alkylisethionates $C_8$-$C_{22}$ or sodium alkylsulfates $C_8$-$C_{22}$ or even alkyl-D-galactoside uronates with the following formula:

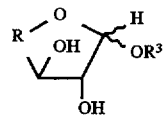

$R^3$ being a linear or branched alkyl radical from 6 to 22 carbon atoms and preferably from 8 to 16 carbon atoms, a hydrocarbonic radical having from 1 to 4 ethylenic non-saturations and from 6 to 22 atoms of carbon or one of these radicals substituted by 1 to 3 substituents on different carbon atoms from hydroxy, halogen or trifluoromethyl, R being

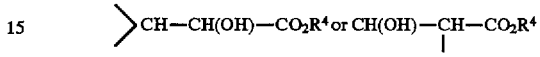

of which the carbon carrying the hydroxy group is not linked to the endocyclic oxygen atom. $R^4$ being hydrogen, an alkaline metal or alkaline-earth metal atom or a quaternary ammonium group.

Various constituents may also be added to these compositions in order to reduce irritation or damage to the skin, such as alkaline metal salts or isethionates, or to moisturize the skin, such as certain carbohydrates (glycerol, sorbitol, for example), polyethylene glycols or polypropylene glycols, alcoxylated derivatives of sugar, or their derivatives (methyl glucose for example), water-soluble or water-dispersible polymers such as collagen or certain non-allergenic derivatives of animal or vegetable proteins (for example wheat protein hydrolysates), natural hydrocolloids (guar, carob or tara gums), products obtained from the fermentation process such as xanthene gum and the derivatives of these polycarbohydrates such as modified cellulose (for example Hydroxyethylcellulose, carboxymethylcellulose, cationic cellulose such as POLYMER JR® marketed by UNION CARBIDE), guar or carob derivatives such as their cationic derivatives (JAGUAR C13S®, JAGUAR C162® marketed by RHONE-POULENC) or non-ionic derivatives (for example hydroxypropylguar), anionic derivatives (carboxymethylguar) or mixed non-ionic/anionic derivatives such as carboxy-hydroxypropyl-guars or non-ionic/cationic derivatives. Instead of or in addition to the above, synthetic polymers such as polyacrylates or synthetic cationic polymers, known generically as "Polyquaternium", for example MIRAPOL A15® or MIRAPOL 550® produced by the RHONE-POULENC company may also be added.

Another advantageous addition to these compounds would be metal sequestering agents, more specifically calcium sequestering agents such as citrate ions or emollient agents such as silicones or fatty oils or substances used for this purpose in the cosmetic industry (mineral oils, fatty acid esters, triglycerides, silicones . . . ). To these ingredients are generally added one or more perfumes, colorants and/or opacifying agents such as pigments (titanium oxide particles). Bactericides or fungicides may also be added to the compound in order to disinfect the skin.

In a toilet tablet which is mainly formed from soaps made from monocarboxylic fatty acids (sodium, potassium, mono-, di- or tri-ethanolammonium salts), the content of fatty acid soaps is generally more than 25% by weight of the formulation, more specifically from 30% to 95% by weight.

Where the principle constituents of the toilet tablet are not fatty acid soaps, the formulation includes from 0% to 50% by weight and preferably from 1% to 40% of these fatty acid soaps.

The compositions of toilet tablets may also contain from 0% to 95%, and preferably from 0% to 60% surface active agents other than soaps, in particular C8–C22 alkyl or alkyenyl isethionates, alkylamidopropylbetaines, alkylamphoacetates, -diacetates, -propionates or -dipropionates used to reduce the irritation which may be caused by the other surface active agents, mainly the anionic surface active agents.

From 1% to 150% of the free fatty acids C8–C22 may also be used in the compositions of soap as superfatting agents or in order to modify the appearance and the creaminess of the foam during washing.

These compositions may also contain waxes such as paraffin waxes, natural waxes such as beeswax, ozocerite or silicone waxes. These waxes may be advantageously used in order to improve the appearance, behavior, processability and storage-life of toilet tablets.

The cosmetic composition may be a foam bath containing from 5% to 40% of a detergent base, which itself contains more than 50% derivatives or a mixture of derivatives according to the invention, and admixtures. The other constituents of the detergent base are the conventional compounds used for these applications as listed above.

The cosmetic composition may be a shower gel containing from 5% to 35% of a detergent base, which itself contains at least 50% derivatives or a mixture of derivatives according to the invention and admixtures.

The cosmetic composition may be a mild liquid soap, containing from 5% to 30% by weight, and preferably 5% to 20% of the derivative according to the invention and from 95% to 70% by weight, preferably 95% to 80% by weight of excipients. These excipients may also be surfactants other than those of the invention.

The cosmetic composition may be a skin care product, in particular for the face, mainly by the incorporation of the derivatives according to the invention, which form a gel type structure for concentrations of water above 60% and preferably above 90%.

The cosmetic composition may be a shampoo, in particular a mild shampoo for frequent use. It contains from 5% to 35% by weight of a detergent base of which, preferably, 10% to 75% is formed from a derivative or mixture of derivatives according to the invention and from 95% to 65% admixtures.

The shampoos and more generally the detergent compositions for personal hygiene use may contain in addition to the non-ionic surfactants according to the invention, the usual additives which are present in this type of preparation. In particular these may include:

anionic surface active agents such as water-soluble salts of alkylsulfates, alkylethersulfates, alkylisethionates and alkylsulfosuccinates or alkylsuccinamates, alkylsarcosinates, alkyl derivatives of protein hydrolysates, acylaspertates, lipid sophoroses, or even alkyl-D-galactoside uronates with the formula:

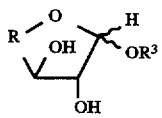

$R^3$ being a linear or branched alkyl radical from 6 to 22 carbon atoms and preferably from 8 to 16 carbon atoms, a hydrocarbonic radical having from 1 to 4 ethylenic non-saturations and from 6 to 22 atoms of carbon or one of these radicals substituted by 1 to 3 substituents on different carbon atoms chosen from hydroxy, halogen or trifluoromethyl, R being

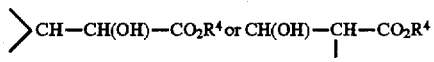

of which the carbon carrying the hydroxy group is not linked to the endocyclic oxygen atom. $R^4$ being hydrogen, an alkaline metal or alkaline-earth metal atom or a quaternary ammonium group;

amphoteric or zwitterionic surface active agents such as alkyl betaines, alkyl amidopropylbetaines, derivatives of imidazoline, such as alkylamphoacetates, alkylamphodiacetates, alkylamphopropionates, alkylamphodipropionates, alkyl sultaines or alkylamidopropylhyroxysultaines;

non-ionic surface active agents such as polyoxyethylene derivatives of aliphatic or arylaliphatic alcohols C8–C22, alkylpolysaccharides with a hydrophobic group C6–C30, and preferably C10–C16 and a polysaccharide group, for example polyglycoside, as hydrophile group together with 1 to 3 sugar units, alkyl derivatives of amino-sugars, such as alkylglucamides produced by the reaction of amidation of a fatty acid on N-methylglucamine;

amides derived from fatty acids generally used for their power to improve the foam generating properties of the compositions or to increase the viscosity of the said compositions;

cationic conditioning agents (to make combing and styling easier, to improve the feel and volume of the hair) such as synthetic cationic polymers, for example MIRAPOL AD® or PIRAPOL A550® marketed by RHONE-POULENC, natural cationic polymers, for example cationic guar derivatives (JAGUAR C135®, JAGUAR C162® marketed by RHONE-POULENC) or cationic cellulose derivatives (POLYMER JR400® marketed by UNION CARBIDE);

organopolysiloxanes used on their own or in solution in one of the usual solvents (low mass silicone oils, highly branched paraffin oils, fatty esters, for example of the isopropyl palmitate type . . . ), as conditioning or brightening agents;

amphoteric polymers such as, for example, dimethyldiallylammonium or diethyldiallylammonium chloride and acrylic acid copolymers;

anti-dandruff agents such as pyridinethiones, more specifically zinc pyridinethione, compounds based on selenium such as selenium sulfide or OCTOPYROX® marketed by HOECHST;

pesticide agents (against lice), such as LINDANE or other pyrethrines used for this purpose.

These compositions may also contain agents which modify the appearance or viscosity of the formulations such as pearlizing compounds based on polyethylene glycol stearate or polymers to improve viscosity or stability such as CARBOPOL® marketed by GOODRICH, hydrocolloids and their derivatives such as guar or modified guars, carob, xanthane gum, cellulose derivatives (hydroxyethylcellulose, carboxymethylcellulose).

Conventional shampoo compositions containing the non-ionic surfactants according to the invention may be formed from (percentages by weight):

| | |
|---|---|
| alkyl pentosides according to the invention | 1%–15% |
| anionic surface active agent | 0%–15% |
| amphoteric surface active agent | 0%–10% |
| fatty acid alkanolamide | 0%–5% |
| thickening agent | 0%–5% |
| conditioning agent | 0%–3% |
| perfume | 0%–2% |
| preservative | 0%–2% |
| anti-dandruff agent | 0%–2% |
| water | making up to 100% |

The non-ionic surfactants according to the invention may also be used in formulations where it is necessary to maintain fine solids in suspension in water, such as agrochemical active materials (herbicides, insecticides, fungicides . . . ) which are known by the generic term of "concentrated suspensions."

In addition to a dispersive surfactant, concentrated suspensions contain other additives such as those described in the commercial brochure entitled, "Auxiliaries for Agrochemical Formulations" edited by RHONE-POULENC GERONAZZO SPA. These may include, for example, a wetting surfactant, taken from the alkyl derivatives of arylaliphatic alcohols, isopropylnaphthalene sulfonate marketed under the name of SUPRAGIL WP® by RHONE-POULENC GERONAZZO, dialkyl sulfosuccinates such as sodium di-ethyl-2-hexyl sulfosuccinates, dispersant polymers such as polyacrylic acids and their salts, malic-diisobutylene anhydride (or acid) copolymers and their salts such as GEROPON T36® (RHONE-POULENC GERONAZZO), condensed sodium methylnaphthalene sulfonates such as SUPRAGIL MNS90® (RHONE-POULENC GERONAZZO), dispersant polymers derived from lignin such as sodium or calcium lignosulfonates or other dispersant surfactants such as alcoxylated derivatives, possibly sulfated or phosphated tristyrylphenols. In addition, these formulations may contain antifreeze additives such as propyleneglycol and thickening additives which modify the rheological behavior of the suspension such as xanthane gum, cellulose derivatives (carboxymethylcellulose), guar gum or its derivatives, clays or modified clays such as bentonite and bentones.

The active materials which may be formed in this way generally have a melting point higher than 45° C. and preferably higher than 60° C. and water solubility of less than 10 g/l, preferably less than 1 g/l. The active materials for crop protection involved are herbicides, fungicides and insecticides, such as those described in *The Pesticide Manual* (9th edition, C. R. WORKLING and R. J. HANCE, eds, published by The British Crop Protection Council) and conform to the criteria set out above.

The following examples will help to illustrate the invention.

EXAMPLE 1

326 g of de-starched dried bran with a dry material content of 92%, including 0.2% starch, 11.5% proteins and 46% pentosans, was brought into contact with 700 g of a 1.8% hydrochloric acid solution. The reaction medium was homogenized in a reaction vessel, shaken then brought to a temperature of 107° C. for 30 minutes. After the thermal shock, the mixture was pressed on a CARVER laboratory press in order to separate the pulp 1 from the juice 1. The solid material content of the collected juice and pulp was 13.8% and 50% respectively. The juice was demineralized by ion exchange on a strong cationic resin (IRA 200) and a weak anionic resin (IRA 945). The juice was then concentrated to up to 72% dry material by evaporation of the water at reduced pressure; the composition obtained is set out in the following table:

| | JUICE 1 |
|---|---|
| Dry material (%) | 72.0 |
| L-Arabinose/ Dry material (%) | 29.5 |
| D-Xylose/Dry material (%) | 58.4 |
| Other sugars/ Dry material (%) | 11.2 |
| Pentoses/Dry material (%) | 84.3 |

The juice had a neutral sugar purity of 95.5%, the pentoses representing 84.3% of the dry material.

20 g of this juice was then suspended in 25 g of n-butanol with the addition of 0.26 g of an acid catalyst. The reaction medium was heated to 80° C and the water was eliminated during the reaction. Following this 31 g of fatty alcohol (decanol: 85%, dodecanol 15%) was added at the same temperature and the butanol was eliminated under reduced pressure. The acidity of the medium was neutralized by a solution of saturated sodium hydrogencarbonate to a pH of 7 to 8. The excess fatty alcohols were eliminated by evaporation under reduced pressure (1 to 5 mb) at a temperature of 140°–160° C. The residue (21 g) was in the form of a paste containing less than 2% residual fatty alcohol. This was made into a 70% solution with water and bleached using hydrogen peroxide.

EXAMPLE 2

326 g of de-starched dried bran with a dry material content of 92%, including 0.2% was starch, 11.5% proteins and 46% pentosans, was brought into contact with 700 g of a 1.8% hydrochloric acid solution. The reaction medium was homogenized in a reaction vessel, shaken then brought to a temperature of 107° C. for 30 minutes. After the thermal shock, the mixture was pressed on a CARVER laboratory press in order to separate the pulp 1 from the juice 1. The solid material content of the collected juice and pulp was 13.8% and 50% respectively. The composition of the juice is set out in the following table:

| | JUICE 1 |
|---|---|
| Dry material (%) | 13.8 |
| L-Arabinose/ Dry material (%) | 25.8 |
| D-Xylose/Dry material (%) | 44.0 |
| Other sugars/ Dry material (%) | 12.3 |
| Pentoses/Dry material (%) | 69.8 |

The purity of the pentoses in the juice was 82.1%, the pentoses representing 69.8% of the dry material. This juice was then concentrated to a dry material content of 49% by evaporation of the water under reduced pressure.

50 g of this juice was then suspended in 96 g of fatty alcohols (octanol: 50%, decanol: 50%) containing 2.5 g of surfactant dry material as described in Example 1. The reaction medium was heated to 80° C. under reduced pressure (50 mb) and after 5 hours of reaction the acidity of this medium was neutralized by a solution of saturated sodium hydrogencarbonate to a pH of 7 to 8. The excess fatty alcohols were eliminated by evaporation under reduced pressure (1 mb) at a temperature of 120°–150° C. The residue obtained (32 g) contained less than 1% residual fatty alcohol.

EXAMPLE 3

The process was carried out in accordance with the description set out in Example 2, with the exception that the octyl-decyl pentosides were purified by chromatography in a Merck 60H silica gel column; eluent; methylene chloride, then methylene/methanol chloride (9/1, v/v). Then 15.3 g of pentosides was obtained in the form of a paste containing less than 0.5% residual fatty alcohol.

EXAMPLE 4

159 kg of de-starched bran with a dry material content of 36% (containing 0.3 kg of starch, 6.7 kg of proteins and 25 kg of pentosans), was brought into contact with 149 kg water and 6.0 kg of sulfuric acid at 95%. The reaction medium was homogenized in a reaction vessel, shaken then brought to a temperature of 140° C. by a steam jet (44 kg) for 30 minutes. After the thermal shock, the mixture was pressed on a helicoidal screw press which decreases in section from the inlet to the outlet, equipped with slotted hole screen which are perpendicular to the axis of the press. The width of the slots is from 0.5 to 0.25 mm. The feed pressure of the presses is from 0.1 to $0.2 \cdot 10^5$ Pa, and the maximum pressure to which the bran is subjected in the narrowest part is $5.10^5$ Pa. The pulp 1 (79 kg) was then separated from the juice 1 (279 kg). The compositions of the juice 1 and pulp 1 are set out in the following table:

|  | Pulp 1 | Juice 1 |
|---|---|---|
| Dry material (%) | 38.9 | 12.9 |
| Starch/Dry material (%) | 0 | 0.8 |
| Proteins/Dry material (%) | 10 | 10 |
| Pentose equivalents/Dry material (%) | 11.6 | 70 |

The pulp 1 was collected immediately after leaving the press by a pump and diluted in line with 236 l of water. It was then subjected to a second pressing process, identical to the first, from which a further 2 fractions were obtained; the juice 2 (262 kg) and the pulp 2 (54 kg). Their compositions are set out in the following table:

|  | Pulp 1 | Juice 1 |
|---|---|---|
| Dry material (%) | 39.1 | 3.7 |
| Starch/Dry material (%) | 0 | 0 |
| Proteins/Dry material (%) | 11.9 | 6 |
| Pentose equivalents/Dry material (5) | 4.8 | 25 |

The fractions of juice 1 and 2 were mixed together, and 22 kg of milk of lime with 20% dry material was added. After centrifuging in a self-cleaning plate centrifuge, a clear juice 3 was obtained (534 kg) from which the insoluble substances and pastes (28.1 kg) had been removed. The content of materials is set out in the following table:

|  | Pastes | Clear juice 3 |
|---|---|---|
| Dry material (%) | 18.0 | 8.4 |
| Starch/ | 2 | 0.5 |
| Dry material (%) Proteins/ | 34 | 5.6 |
| Dry material (%) Pentose equivalents/ Dry material (%) | 12 | 60.2 |

The clear juice 3 was then demineralized by ion exchange on a strong cationic resin (IR 200) and a weak anionic resin (IRA 94S). The juice 4 obtained (561 kg with 6% dry material) was then concentrated to 70% dry material by evaporation of the water under reduced pressure; its composition is set out in the following table:

|  | Juice 4 |
|---|---|
| Dry material (%) | 70.0 |
| Starch/Dry material (%) | 0.6 |
| Proteins/Dry material (%) | 1.5 |
| Pentoses/Dry material (%) | 79.7 |

This juice was then suspended in 65 kg of n-butanol with the addition of 0.7 kg of an acid catalyst. The reaction medium was heated to 80° C. and the water was eliminated during the reaction. Following this 73.3 kg of fatty alcohol (decanol: 85%, dodecanol 15%) was added at the same temperature and the butanol was eliminated under reduced pressure. The acidity of the medium was neutralized by a 32% aqueous soda solution. The excess fatty alcohols were eliminated by evaporation under reduced pressure (1 to 5 mb) at a temperature of 140°–160° C. The residue (58.8 kg) was in the form of a paste containing less than 1% residual fatty alcohol. This was made into a 60% solution with water and bleached with 3.5 kg of a 50% solution of hydrogen peroxide.

EXAMPLE 5

109 kg of ground straw with a dry material content of 92% (containing 33.5 kg cellulose, 3.0 kg of proteins, 25 kg of pentosans and 16.5 kg of lignin), was brought into contact with 805 kg of water and 10.5 kg of a 95% solution of sulfuric acid. The reaction medium was homogenized in a reaction vessel, shaken then brought to a temperature of 140° C. by a steam jet (91 kg) for 30 minutes. After the thermal shock, the mixture was pressed on a helicoidal screw press which decreases in section from the inlet to the outlet, equipped with slotted hole screens which are perpendicular to the axis of the press. The width of the slots is from 0.5 to 0.25 mm. The feed pressure of the presses is from 0.1 to $0.2 \cdot 10^5$ Pa, and the maximum pressure to which the straw is subjected in the narrowest part is $5.10^5$ Pa. The pulp 1 (183 kg) was then separated from the juice 1 (832 kg). The compositions of the juice 1 and pulp 2 are set out in the following table:

|  | Pulp 1 | Juice 1 |
|---|---|---|
| Dry material (%) | 41.5 | 4.3 |
| Cellulose/Dry material (%) | 43.1 | 2.0 |
| Proteins/Dry material (%) | 3.0 | 2.0 |
| Lignin/Dry materials (%) | 23.7 | 1.1 |

-continued

|  | Pulp 1 | Juice 1 |
|---|---|---|
| Pentose equivalents/ Dry material (%) | 5.3 | 62.5 |

The pulp 1 was collected immediately after leaving the press by a pump and diluted in line with 548 l of water. It was then subjected to a second pressing process, identical to the first, from which a further 2 fractions were obtained; the juice 2 (621 kg) and the pulp 2 (110 kg). Their compositions are set out in the following table:

|  | Pulp 2 | Juice 2 |
|---|---|---|
| Dry material (%) | 50 | 3.4 |
| Cellulose/ Dry material (%) | 60.0 | 0 |
| Proteins/ Dry material (%) | 1.3 | 7.6 |
| Lignin/ Dry materials (%) | 32.7 | 0 |
| Pentose equivalents/ Dry material (%) | 1.0 | 16.1 |

The fractions of juice 1 and 2 were mixed together, and 65 kg of milk of lime with 20% dry material was added. After centrifuging in a self-cleaning plate centrifuge, a clear juice 3 was obtained (1352 kg) from which the insoluble substances and pastes (167.1 kg) had been removed. The content of materials is set out in the following table:

|  | Pastes | Juice 3 |
|---|---|---|
| Dry material (%) | 10 | 3.0 |
| Cellulose/ Dry material (%) | 4.1 | 0 |
| Proteins/ Dry material (%) | 1.8 | 5.0 |
| Lignin/ Dry material (%) | 2.3 | 0 |
| Pentose equivalents/ Dry material (%) | 3.0 | 63.2 |

The clear juice 3 was then demineralized by ion exchange on a strong cationic resin (IR 200) and a weak anionic resin (IRA 94S). The juice 4 obtained (1420 kg with 2.2% dry material) was then concentrated to 70% of the dry material by evaporation of the water under reduced pressure; its composition is set out in the following table:

|  | Juice 4 |
|---|---|
| Dry material (%) | 70.0 |
| Cellulose/Dry material (%) | 0.0 |
| Proteins/Dry material (%) | 1.5 |
| Pentoses/Dry material (%) | 80.6 |

This juice was then suspended in 60.G kg of n-butanol with the addition of 0.6 kg of an acid catalyst. The reaction medium was heated to 80° C. and the water was eliminated during the reaction. Following this 68.2 kg of fatty alcohol (decanol: 85%, dodecanol: 15%) was added at the same temperature and the butanol was eliminated under reduced pressure. The acidity of the medium was neutralized by a 32% aqueous soda solution. The excess fatty alcohols were eliminated by evaporation under reduced pressure (1 to 5 mb) at a temperature of 140°–160° C. The residue (55.5 kg) was in the form of a paste containing less than 1% residual fatty alcohol. This was made into a 70% solution with water and bleached with 3.3 kg of a 50% hydrogen peroxide solution.

EXAMPLE 6

217 kg of ground straw with a dry material content of 92% was brought into contact with 185 kg of water, 455 kg of the juice 2 from Example 5, 240 kg of juice 1 from Example 5 and 15 kg of a 95% solution of sulfuric acid. The reaction medium was homogenized in a reaction vessel, shaken then brought to a temperature of 140° C. for 30 minutes. After the thermal shock, the mixture was pressed on a STORD MS 35 double screw press. The pulp 1 was then separated from the juice 1 (480 kg). The composition of the juice 1 is set out in the following table:

|  | Juice 1 |
|---|---|
| Dry material (%) | 15 |
| Pentoses/Dry material (%) | 55 |

The pulp 1 was collected immediately after leaving the press by a pump and diluted in line with 450 l of water. It was then subjected to a second pressing process, identical to the first, from which a further two fractions were obtained; the juice 2 (455 kg) and the pulp 2. The juice 2 was then returned for hydrolysis of a new batch of straw.

The juice 1 was mixed with 50 ml of milk of lime at 180 g/l per liter of juice. After centrifuging in a self-cleaning plate centrifuge, a clear juice 3 was obtained from which the insoluble substances and pastes had been removed.

The clear juice 3 was then demineralized by ion exchange on a strong cationic resin (IR 200) and a weak anionic resin (IRA 945). The juice 4 obtained was then concentrated to 75% of the dry material by evaporation of the water under reduced pressure; its composition is set out in the following table:

|  | Juice 4 |
|---|---|
| Dry material (%) | 75.0 |
| Pentoses (kg) | 45 |
| Proteins/Dry material (%) | 1.5 |
| Pentoses/Dry material (%) | 90 |

This juice was then suspended in 83 kg of n-butanol containing 0.5 kg of an acid catalyst. The reaction medium was heated to 80° C. and the water eliminated during the reaction. Following this 93 kg of fatty alcohol (octanol 50%, decanol 50%) was added at the same temperature and the butanol was eliminated under reduced pressure. The acidity of the medium was neutralized by a 32% aqueous soda solution. The excess fatty alcohols were eliminated by evaporation under reduced pressure (1 to 5 mb) at a temperature of 120°–140° C. The residue (83.6 kg) was in the form of a paste containing less than 1% residual fatty alcohol. This was made into a 70% solution with water and bleached with 5 kg of a 50% solution of hydrogen peroxide.

EXAMPLE 7

A suspension of coarse bran containing 20% dry materials (100 g of dry bran material per 500 g of suspension) was prepared in a sulfuric acid solution (10% $H_2SO_4$/dry bran material). The reaction medium was homogenized in a reaction vessel, shaken then brought to a temperature of 130° C. for 30 minutes. After the thermal shock, the mixture was pressed on a MARREL press to separate the pulp 1 from the juice 1. The dry material content of the collected juice and pulp was 17.37% and 53.0% respectively. The composition of the juice 1 is set out in the following table:

|  | Juice 1 |
| --- | --- |
| Dry material (%) | 17.4 |
| Pentoses/Dry material (%) | 49 |

The juice 1 was mixed with milk of lime (16.4% v/v) with 30% dry material. After centrifuging in a self-cleaning plate centrifuge, a clear juice 2 was obtained from which the insoluble substances and pastes had been removed.

The clear juice 2 was then demineralized by ion exchange on a strong cationic resin (IR 200) and a weak anionic resin (IRA 94S). The juice 3 obtained was then concentrated to 75% of the dry material by evaporation of the water under reduced pressure; its composition is set out in the following table:

|  | Juice 3 |
| --- | --- |
| Dry material (%) | 75.0 |
| Proteins/Dry material (%) | 1.5 |
| Pentoses/Dry material (%) | 90 |

100 g of this juice was then suspended in 114 g of nobutanol containing 1.3 g of an acid catalyst. The reaction medium was heated to 100° C. and the water eliminated during the reaction. Following this 156 g of fatty alcohol (dodecanol) was added at the same temperature and the butanol was eliminated under reduced pressure. The acidity of the medium was neutralized by a 32% aqueous soda solution. The excess fatty alcohols were eliminated by evaporation under reduced pressure (1 to 5 mb) at a temperature of 160°–170° C. The residue (104 g) was in the form of a paste containing less than 1% residual fatty alcohol. This was made into a 50% solution with water and bleached with 6 g of a 50% solution of hydrogen peroxide.

EXAMPLE 8

4762 g of wheat fibers with a dry material content of 21% was brought into contact with 6138 g of water and 100 g of a 95% solution of sulfuric acid. The reaction medium was homogenized in a reaction vessel, shaken then brought to a temperature of 140° C. by a steam jet (1620 g) for 30 minutes. After the thermal shock, a juice 1 (12620 g) was obtained having a dry material content of 8.7%.

This juice 1 was mixed with 505 g of milk of lime with 18% dry material. After centrifuging in a self-cleaning plate centrifuge, a clear juice 2 was obtained from which the insoluble substances and pastes had been removed.

The clear juice 2 was then demineralized by ion exchange on a strong cationic resin (IR 200) and a weak anionic resin (IRA 94S). The juice 3 obtained was then concentrated to 70% of the dry material by evaporation of the water under reduced pressure; its composition is set out in the following table:

|  | Juice 3 |
| --- | --- |
| Dry material (%) | 70.0 |
| Mass (g) | 1139 |
| Pentoses (g) | 702 |
| Proteins/Dry material (%) | 1.5 |
| Pentoses/Dry material (%) | 88 |

This juice was then suspended in 1215 g of n-butanol containing 11.9 g of an acid catalyst. The reaction medium was heated to 105° C. and the water eliminated during the reaction. Following this 1408 g of fatty alcohol (decanol) was added at the same temperature and the butanol was eliminated under reduced pressure. The acidity of the medium was neutralized by a 32% aqueous soda solution. The excess fatty alcohols were eliminated by evaporation under reduced pressure (1 to 5 mb) at a temperature of 140°–160° C. The residue (925 g) was in the form of a paste containing less than lot residual fatty alcohol. This was made into a 70% solution with water and bleached with 60 g of a 50% solution of hydrogen peroxide.

EXAMPLE 9

The juice 3 from Example 8 was then suspended in 1215 g of n-butanol with the addition of 11.9 g of an acid catalyst. The reaction medium was heated to 105° C. and the water was eliminated during the reaction. Following this 1238 g of fatty alcohol (octanol/decanol=1/1) was added at the same temperature and the butanol was eliminated under reduced pressure. The acidity of the medium was neutralized by a 32% aqueous soda solution. The excess fatty alcohols were eliminated by evaporation under reduced pressure (1 to 5 mb) at a temperature of 120°–160° C. The residue (909 g) was in the form of a paste containing less than 1% residual fatty alcohol. This was made into a 70% solution with water and bleached with 60 g of a 50% hydrogen peroxide solution.

EXAMPLE 10

The process was carried out in accordance with the description set out in Example 1, with the exception that a mixture of hexadecanol and octadecanol was used as the fatty alcohol and the alkyl pentosides were purified by chromatography in a Merck 60H silica gel column; eluent; methylene chloride, then methylene/methanol chloride (9/1, v/v). This gave 23 g of pentosides containing less than 0.5% residual fatty alcohol.

EXAMPLE 11

The process was carried out in accordance with the description set out in Example 1, with the exception that a mixture of hexadecanol and octadecanol was used as the fatty alcohol and that the fatty alcohols were not removed at the end of the synthesis. This gave 59 g of pentosides containing 51% residual fatty alcohol.

EXAMPLE 12

Relative reactivity of D-xylose, L-arabinose and D-glucose

The sugar was suspended in 4 equivalents of octanol with a ratio of 3% by mass of sulfuric acid to sugar. The water from the reaction was eliminated under reduced pressure of 90 mb as it was formed. The progress of the reaction was monitored by GC after silylation of the reaction medium. The results are given in the following table.

| Sugars | T = 90° C. Reaction Time | Notes |
|---|---|---|
| D-xylose | 60 min | transparent medium |
| L-arabinose | 90 min | transparent medium |
| D-glucose | 19 h | brown solid medium |
| L-arabinose/ D-glucose 80/20 | 3 h | transparent brown medium |
| Bran syrup from Example 4 (juice 4) | 3 h | transparent, slightly colored medium |

Comparative glycosidation of the pentoses and hexoses which constitute the bran syrups Under the reaction conditions described above, it is clear that pentoses react more quickly than glucose during glycosylation. In order to activate all the glucose in several hours it would be necessary to increase the reaction temperature to above 90° C. We have also demonstrated that if the reaction is carried out using L-arabinose and D-glucose in a ratio of 80/20, the glucose is activated more quickly.

EXAMPLE 13

Foaming powers of alkyl pentosides according to the invention
$R^1 = C8, C10, C12$

| Surfactant | Fatty alcohol | Concentration (%) | Volume of foam (ml) |
|---|---|---|---|
| Example 1 | C10–C12 | 0.1 | 460 |
| | | 1.0 | 540 |
| Example 2 | C8–C10 | 0.1 | 355 |
| | | 1.0 | — |
| Example 3 | C8–C10 | 0.1 | 360 |
| | | 1.0 | 420 |
| Example 4 | C10–C12 | 0.1 | 500 |
| | | 1.0 | 530 |
| Example 5 | C10–C12 | 0.1 | 490 |
| | | 1.0 | 510 |
| Example 6 | C8–C10 | 0.1 | 495 |
| | | 1.0 | 520 |
| Example 7 | C12 | 0.1 | 390 |
| | | 1.0 | — |
| Example 8 | C10 | 0.1 | 505 |
| | | 1.0 | — |
| Example 9 | C8–C10 | 0.1 | 460 |
| | | 1.0 | 560 |

EXAMPLE 14

Comparative measurements of foaming powers of alkyl pentosides according to the invention
$R^1 = C8-C10, C10, C10-C12, C12$

| Surfactant | Alkyl chain | Concentration (%) | Volume of foam (ml) |
|---|---|---|---|
| Example 4 | C10–C12 | 0.1 | 500 |
| | | 1.0 | 530 |
| Example 5 | C10–C12 | 0.1 | 490 |
| | | 1.0 | 510 |
| Example 6 | C8–C10 | 0.1 | 495 |
| | | 1.0 | 520 |
| Example 8 | C10 | 0.1 | 505 |
| | | 1.0 | — |
| Example 9 | C8–C10 | 0.1 | 460 |
| | | 1.0 | 560 |
| Dodecyl betaine | C12 | 0.1 | 400 |
| | | 1.0 | — |
| LES | C12 | 0.1 | 420 |
| | | 1.0 | 460 |
| ORAMIX CG 110 | C8–C10 | 0.1 | 460 |
| | | 1.0 | — |
| PLANTAREN 2000 | C8–C16 | 0.1 | 465 |
| | | 1.0 | — |

EXAMPLE 15

Stability of foam from alkyl pentoside according to the invention
$R^1 = C8-C10, C10, C12, C10-C12$ 0.1% Surfactant

| Time (min) | Example 4 | Example 5 | Example 6 | Example 8 | Example 9 |
|---|---|---|---|---|---|
| 0 | 500 | 490 | 495 | 505 | 460 |
| 1 | 500 | 485 | 490 | 500 | 455 |
| 2 | 490 | 480 | 485 | 495 | 450 |
| 5 | 480 | 470 | 470 | 475 | 425 |
| 10 | 410 | 450 | 430 | 440 | 395 |
| 15 | 370 | 415 | 400 | 400 | 380 |
| 20 | 350 | 410 | 370 | 375 | 365 |

EXAMPLE 16

Comparative measurements of the stability of foam from alkyl pentosides according to the invention
$R^1 = C8-C10, C10, C12, C10-C12$

| Time (min) | Ex. 4 | Ex. 8 | Dodecyl betaine | LES | ORAMIX CG 110 | PLANTAREN 2000 |
|---|---|---|---|---|---|---|
| 0 | 500 | 505 | 400 | 460 | 460 | 465 |
| 1 | 500 | 500 | 390 | 430 | 455 | 460 |
| 2 | 490 | 495 | 390 | 430 | 455 | 460 |
| 5 | 480 | 475 | 360 | 370 | 440 | 450 |
| 10 | 410 | 440 | 330 | 300 | 430 | 430 |
| 15 | 370 | 400 | 310 | 80 | 415 | 420 |
| 20 | 350 | 375 | 290 | 0 | 410 | 415 |

EXAMPLE 17

Comparative measurements of surface tensions at a concentration higher than the CMC of alkyl pentosides according to the invention
$R^1 = C8-C10, C10-C12$

| Surfactant | $_fCMC$ (mN/m) |
|---|---|
| Glycosides from Example 1 | 26.3 |
| Glycosides from Example 2 | 26.6 |
| Glycosides from Example 3 | 25.7 |
| Glycosides from Example 4 | 26.2 |

-continued

Comparative measurements of surface tensions at a concentration higher than the CMC of alkyl pentosides according to the invention
$R^1 = C8-C10, C10-C12$

| Surfactant | CMC (mN/m) |
|---|---|
| Glycosides from Example 5 | 26.4 |
| Glycosides from Example 6 | 26.7 |
| Glycosides from Example 7 | 26.5 |
| Glycosides from Example 8 | 26.5 |
| Glycosides from Example 9 | 27.5 |
| LES | 35 |
| SDBS | 30 |
| ORAMIX NS 100 | 27.3 |
| PLANTAREN 2000 | 29.7 |

EXAMPLE 18

Examples of foaming preparations:

Shampoos:

| | |
|---|---|
| Sclerotium gum | 1.15 g |
| Surfactants from Example 5 | 10 g |
| Colorants, perfumes | qs |
| Fatty acid diethanolamide from soya | 3 g |
| Water | qsp 100 g |

Shower gel:

| | |
|---|---|
| Surfactants from Example 6 | 10 g |
| Fatty acid diethanolamide from soya | 7 g |
| Colorants, perfumes | qs |
| Water | qsp 100 g |

EXAMPLES 19 TO 21

FORMULAE FOR DETERGENT IN POWDER FORM

| | 19 | 20 | 21 |
|---|---|---|---|
| Lauryl benzene sulfonate | 2 | 0 | 5 |
| Decyl D-galactoside-sodium uronate | 10 | 20 | 10 |
| olefin sulfonate | 0 | 10 | 0 |
| Dodecyl D-galactoside-sodium uronate | 4 | 4 | 0 |
| Octyl D-galactoside octyl uronate | 0 | 4 | 0 |
| Dodecyl D-galactoside dodecyl uronate | 0 | 0 | 2 |
| Pentosides from Example 1 | 2 | 2 | |
| Silicone oil | 2 | 2 | 0.2 |
| Zeolite 4 A | 25 | 20 | 25 |
| Sodium nitrilotriacetate | 8 | 15 | 10 |
| Sodium carbonate | 8 | 15 | 10 |
| Sodium citrate | 1 | 0 | 0 |
| Clay | 0 | 4 | 3 |
| Sodium perborate | 20 | 4 | 3 |
| Ethylene diamine tetraacetyl | 1 | 0 | 0 |
| Ethylene diamine tetraacetate | 0.5 | 0 | 0 |
| Sodium carboxymethyl cellulose gel | 1 | 2 | 0.3 |
| Enzymes | 0.5 | 0.4 | 1 |
| Optical brighteners | 0.2 | 0.5 | 0.1 |
| Sodium silicate | 4 | 10 | 10 |
| Perfumes | qs | qs | qs |
| Water | remainder | remainder | remainder |

EXAMPLES 22 TO 24

LIQUID DETERGENT FORMULAS

| | 22 | 23 | 24 |
|---|---|---|---|
| Alkyl benzene sulfonate | 5 | 0 | 5 |
| Soaps | 10 | 0 | 15 |
| Fatty alcohol ether sulfate | 0 | 2 | 5 |
| Dodecyl D-galactoside-sodium uronate | 0 | 20 | 5 |
| Compounds from Example 2 | 10 | 3 | 10 |
| Poly alkyl ether (ethylene glycol) | 10 | 0 | 10 |
| Decyl D-galactoside-sodium uronate | 5 | 10 | 0 |
| Dimethylammonium chloride | 0 | 0 | 4 |
| Fatty acid alkanolamide | 1 | 0 | 0 |
| Proteases | 0.5 | 0.5 | 0 |
| Sodium citrate | 2 | 4 | 5 |
| Zeolites | 0 | 20 | 0 |
| Sodium silicate | 1 | 0 | 0 |
| Ethanol/propylene glycol | 10 | 8 | 13 |
| Polycarboxylates | 0 | 2 | 5 |
| Optical brighteners | qs | qs | qs |
| Stabilizers (mono ethanolamide) | 3 | 0 | 3 |
| Perfumes | qs | qs | qs |
| Colorants | qs | qs | qs |
| Water | 12.5 | 30 | 28 |

EXAMPLES 25 TO 28

WASHING UP LIQUID FORMULATIONS

| | 25 | 26 | 27 | 28 |
|---|---|---|---|---|
| Decyl D-galactoside-sodium uronate | 0 | 0 | 0 | 10 |
| Dodecyl D-galactoside-sodium uronate | 15 | 20 | 0 | 10 |
| Compounds from Example 3 | 5 | 2 | 15 | 5 |
| Ethyoxylated fatty acid monoethanolamide | 5 | 5 | 5 | 0 |
| Lauryl diethanolamide | 0 | 0 | 3 | 10 |
| Sodium polyoxyethylene lauryl sulfate | 0 | 0 | 10 | 0 |
| Sodium chloride | 3 | 3 | 0 | 0 |
| Sodium acrylate | 0.2 | 0 | 0 | 0 |
| Ethylenediamine tetraacetic acid (EDTA) | 0.3 | 0 | 0 | 0 |
| Ethanol | 0 | 0 | 0 | 3 |
| Propylene glycol | 0 | 0 | 0.2 | 0 |
| Amine oxide | 0 | 0 | 1 | 0 |
| Perfumes | qs | qs | qs | qs |
| Colorants | qs | qs | qs | qs |
| Preservatives | 0.5 | 0.5 | qs | qs |
| Water | qsp 100 | qsp 100 | qsp 100 | qsp 100 |

EXAMPLES 29 TO 32

MILD LIQUID SOAP FORMULATIONS

| | 29 | 30 | 31 | 32 |
|---|---|---|---|---|
| Compound from Example 4 | 10 | 15 | 10 | 5 |
| Sodium dodecyl d-galactoside | 0 | 0 | 5 | 10 |
| Dodecyl D-galactoside dodecyl uronate | 0 | 2 | 0 | 0 |
| Tetradecyl D-galactoside tetradecyl uronate | 0 | 0 | 0 | 3 |
| Lauryl sodium sulfate | 0 | 5 | 0 | 0 |

-continued

MILD LIQUID SOAP FORMULATIONS

|  | 29 | 30 | 31 | 32 |
|---|---|---|---|---|
| Sodium cocoyl isothionate | 5 | 0 | 0 | 0 |
| Alkyl peptide sodium salt | 0 | 0 | 0 | 3 |
| Wheat protein hydrolysate | 0 | 0 | 2 | 0 |
| Propylene glycol | 0 | 0 | 0 | 4 |
| Sodium chloride | 3 | 2 | 2 | 0 |
| EDTA | 0.3 | 0.3 | 0.3 | 0.3 |
| Cetyl alcohol | 0 | 0 | 0 | 3 |
| Heavy mineral oil | 0 | 0 | 0 | 15 |
| Cocoamidoethanolamide | 5 | 0 | 5 | 0 |
| Hydroxymethyl cellulose | 0 | 0 | 0 | 0.5 |
| Preservatives | qs | qs | qs | qs |
| Disinfectants | 0 | 0 | 0 | 0.2 |
| Perfumes | qs | qs | qs | qs |
| Water | qsp 100 | qsp 100 | qsp 100 | qsp 100 |

EXAMPLES 33 TO 36

SHAMPOO FORMULATIONS

|  | 33 | 34 | 35 | 36 |
|---|---|---|---|---|
| Dodecyl D-galactoside sodium uronate | 0 | 0 | 5 | 0 |
| Tetradecyl D-galactoside sodium uronate | 10 | 0 | 5 | 5 |
| Lauryl ether disodium sulfosuccinate | 0 | 5 | 0 | 0 |
| 30% Cocoamidopropyl betaine | 5 | 10 | 0 | 5 |
| Fatty acid diethanolamide from Copra | 0 | 0 | 0 | 5 |
| Compounds from Example 2 | 5 | 10 | 10 | 10 |
| Wheat protein hydrolysate | 0 | 0 | 0 | 2 |
| Octadecyl polyethylene glycol | 10 | 0 | 0 | 0 |
| Sodium chloride | 0 | 1.5 | 1.5 | 2 |
| Preservatives | 0.5 | 0.4 | 0.4 | 0.4 |
| EDTA | 0.3 | 0.3 | 0.3 | 0.3 |
| Perfumes | qs | qs | qs | qs |
| Water | qsp 100 | qsp 100 | qsp 100 | qsp 100 |

EXAMPLES 37 TO 38

FOAM BATH FORMULATIONS

|  | 37 | 38 |
|---|---|---|
| Dodecyl D-galactoside-sodium uronate | 5 | 10 |
| Compounds from Example 3 | 15 | 10 |
| Cocoyl monoethanolamide | 5 | 5 |
| Lauryl amidopropyl betaine | 2 | 0 |
| Lauryl amidodimethyl betaine | 0 | 2 |
| Triethylene glycol | 2 | 0 |
| Sweet almond oil | 6 | 5 |
| Ethoxylated sorbitan laurate | 2 | 2 |
| Dioleate of ethoxylated propylene glycol | 0 | 2 |
| Lauryl myristyl 30 E | 2 | 0 |
| EDTA | 0.3 | 0.3 |
| Sodium chloride | 2 | qs |
| Oleyle acrylate | 0 | 2 |
| Preservatives | 0.5 | qs |
| Hexadecanol | 1 | 1 |
| Perfumes | qs | qs |
| Water | qsp 100 | qsp 100 |

EXAMPLES 39 AND 40

SHOWER GEL FORMULATIONS

|  | 39 | 40 |
|---|---|---|
| Decyl D-galactoside sodium uronate | 5 | 0 |
| Tetradecyl D-galactoside sodium uronate | 0 | 5 |
| Hexadecyl D-galactoside sodium uronate | 0 | 1 |
| Compounds from Example 5 | 10 | 10 |
| Lauryl amidopropyl betaine | 2 | 0 |
| Acrylic gel | 0 | 0.2 |
| EDTA | 0.3 | 0.3 |
| Sodium chloride | 3 | 0 |
| Pearlising agents | 0 | 5 |
| Perfumes | 0.2 | 0 |
| Preservatives | 0.5 | 0.5 |
| Water | qsp 100 | qsp 100 |

EXAMPLES 41 TO 46

|  | % |
|---|---|
| Example 41: SHAMPOO | |
| Surfactants from Example 6 | 8 |
| Sodium decyl galacturonate | 4 |
| Methocel 40-202-E | 0.8 |
| Wheat peptides | 0.5 |
| Phenonip* | 0.3 |
| Colorant | qs |
| Perfume | qs |
| Water | qsp 100 |
| Example 42: TONIC LOTION | |
| Surfactants from Example 8 | 1 |
| Sodium hyaluronate | 0.2 |
| Phenonip | 0.5 |
| Cornflower water | 5 |
| Colorant | qs |
| Perfume | qs |
| Water | qsp 100 |
| Example 43: SHOWER GEL | |
| Surfactants from Example 7 | 10 |
| Tegobetaine | 2 |
| Sophorose lipid | 2 |
| Dodecyl galacturonate | 2 |
| Carboxymethyl cellulose sodium salt | 1 |
| Wheat oil | 1 |
| Colorant | qs |
| Perfume | qs |
| Water | qsp 100 |
| Example 44: HAND CREAM | |
| Surfactants from Example 10 | 5 |
| Apiphil | 4 |
| Cellulose | 1 |
| Allantoin | 0.3 |
| Glycerol | 3 |
| Sophorose lipid | 1 |
| Vaseline oil | 3 |
| Vegetable oil | 5 |
| Phenonip | 0.3 |
| Colorant | qs |
| Perfume | qs |
| Water | qsp 100 |
| Example 45: MOISTURIZING CREAM | |
| Tephose 1500 | 3 |
| Hexadecyl sodium galacturonate | 2 |
| Surfactants from Example 11 | 2 |
| Vaseline oil | 5 |
| Wheat oil | 2 |

-continued

|  | % |
|---|---|
| Macadamia oil | 1 |
| Karite nut butter | 2 |
| Sipol C16 | 1.5 |
| Sodium hyaluronate | 0.2 |
| Wheat peptides | 0.3 |
| Phenonip | 0.5 |
| Perfume | qs |
| Colorant | qs |
| Water | qsp 100 |

Example 46: FOAM BATH

|  | % |
|---|---|
| Surfactants from Example 9 | 16 |
| Decyl/dodecyl sodium galacturonate | 4 |
| Dyonil OC/K | 3 |
| NaCl | 2 |
| Wheat oil | 2 |
| Marlamid 1218 | 3 |
| Flower water | 5 |
| Phenonip | 0.3 |
| Perfume | qs |
| Colorant | qs |
| Water | qsp 100 |

Although some preferred embodiments of the invention have been described above by way of example only, it will be understood by those skilled in the field that modifications may be made to the disclosed embodiments without departing from the scope of the invention, which is defined by the appended claims.

We claim:

1. A process for preparing a surface active agent wherein wheat bran, wheat fibre or wheat straw is brought into contact with an aqueous acid solution at a temperature of between 20° and 150° C. for at least 5 seconds in order to obtain an aqueous pentose syrup and solid pulp, separating the solid pulp from the aqueous pentose syrup, the latter having a concentration of 30 to 95% by weight of pentoses, contacting the aqueous pentose syrup with an alcohol of the formula $R^2OH$ in which $R^2$ is a linear alkyl radical having from 1 to 5 carbon atoms at a temperature of between 20° and 150° C. to form a solution of lower alkyl ($C_1$–$C_5$) pentosides, contacting the solution of lower alkyl ($C_1$–$C_5$) pentosides with an alcohol of the formula $R^1OH$ in which $R^1$ is a branched or linear alkyl radical having from 6 to 22 carbon atoms at a temperature of between 20° and 150° C. to form a solution of surface active pentosides, and separating the surface active pentosides from the solution.

2. The process of claim 1, wherein the wheat bran, wheat fibre or wheat straw is brought into contact with said aqueous acid solution for 5 to 90 minutes.

3. The process of claim 1, wherein said aqueous pentose syrup is demineralized by chromatography, electrodialysis, or by passing it through at least one ion exchanger before being brought into contact with the alcohol of formula $R^2OH$.

4. The process of claim 3, wherein said demineralized aqueous pentose syrup is passed through a cation exchange resin, then an anion exchange resin leaving at least 0.02° $H^+$ equivalent per mole of pentoses.

5. The process of claim 3, wherein the solid pulp is separated from the aqueous pentose syrup by pressing followed by centrifuging.

6. The process of claim 5, wherein the aqueous pentose syrup is brought into contact with a chelating salt before being centrifuged.

7. The process of claimed 1, wherein the aqueous pentose syrup is brought into contact with a chelating agent before the solid pulp is separated.

8. The process of claim 1, wherein the separated aqueous pentose syrup contains a significant proportion of pentoses.

9. The process of claim 8, where in said pentoses include D-xylose and L-arabinose.

* * * * *